US006364052B1

(12) United States Patent
McLean

(10) Patent No.: US 6,364,052 B1
(45) Date of Patent: Apr. 2, 2002

(54) EARPLUGS WITH SURFACE ORNAMENTATION

(75) Inventor: Ivan McLean, Portland, OR (US)

(73) Assignee: Ivan McLean, Inc., Portland, OR (US)

( * ) Notice: Subject to any disclaimer, the term of this patent is extended or adjusted under 35 U.S.C. 154(b) by 0 days.

(21) Appl. No.: 09/524,829

(22) Filed: Mar. 14, 2000

(51) Int. Cl.[7] ............................................. A61B 7/02
(52) U.S. Cl. ........................ 181/135; 128/864; 128/865
(58) Field of Search ..................... 181/135; 128/864, 128/865

(56) References Cited

U.S. PATENT DOCUMENTS 5,799,658 A  *  9/1998  Falco ........................... 128/864
D405,173 S  *  2/1999  Falco .......................... D24/106
6,105,715 A  *  8/2000  Knauer ........................ 181/135

FOREIGN PATENT DOCUMENTS

FR  2701840  *  2/1993  ................ 181/135
GB  2172508 A  *  3/1986  ................ 181/135

* cited by examiner

Primary Examiner—Robert E. Nappi
Assistant Examiner—Kim Lockett
(74) Attorney, Agent, or Firm—Ipsolon LLP

(57) ABSTRACT

Noise-reducing earplugs include a configuration and surface ornamentation to resemble a product other than earplugs, or a container for such a product. For example, such earplugs may have a generally cylindrical configuration and appropriate surface ornamentation to resemble can-type containers as are used for beverages (e.g., soft drinks or beer) and other liquid products (e.g., paints, oils, fuel additives, etc.).

6 Claims, 1 Drawing Sheet

EARPLUGS WITH SURFACE ORNAMENTATION

FIELD OF THE INVENTION

The present invention relates to foam or other resiliently expandable earplugs that protect peoples' ears from loud noises and, in particular, to such earplugs that include surface ornamentation to resemble products other than earplugs.

BACKGROUND AND SUMMARY OF THE INVENTION

There are many types of events, such as popular music concerts or motor sport events (e.g., car races), at which spectators are subjected to extremely loud noises. There is also increasing appreciation that such loud noises can cause hearing loss. As a result, many spectators who attend such events bring noise-reducing earplugs to protect their hearing from the loud noises. However, many other people who attend such events fail to bring earplugs with them so that their enjoyment of the event is diminished either by the discomfort of the loud noises or concern that their hearing might be damaged by the loud noises.

In accordance with one implementation of the present invention, noise-reducing earplugs include a configuration and surface ornamentation to resemble a product other than earplugs, or a container for such a product. For example, such earplugs may have a generally cylindrical configuration and appropriate surface ornamentation to resemble can-type containers as are used for beverages (e.g., soft drinks or beer) and other liquid products (e.g., paints, oils, fuel additives, etc.). As a result, earplugs of the present invention provide a unique advertising medium and, when distributed at events that are characteristically loud, could be highly appreciated by attending spectators.

Additional objects and advantages of the present invention will be apparent from the detailed description of preferred embodiments thereof, which proceeds with reference to the accompanying drawings.

DETAILED DESCRIPTION OF PREFERRED EMBODIMENT

Figure 1:
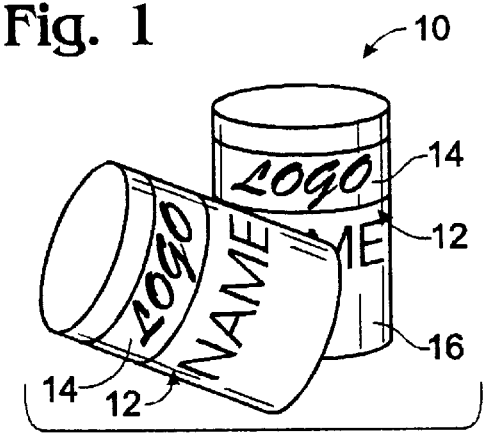
FIG. 1 is an isometric view of a first pair of exemplary earplugs according to the present invention.

FIG. 1 is an isometric view of a pair of exemplary earplugs 10 according to the present invention. Earplugs 10 may be formed of conventional foam or other resiliently expandable material and are sized to be fitted within a person's ear canals to provide noise reduction, as is known in the art. Prior art earplugs generally of this type are available from many suppliers such as, for example, Aearo Company of Indianapolis, Ind. Earplugs 10 are compressed by a person and placed into the person's ear canals where earplugs 10 expand to form a snug fit and to protect the person's ears against loud noises.

In accordance with the present invention, earplugs 10 include a configuration and surface ornamentation 12 (e.g., printed ornamentation) so that earplugs 10 resemble a selected product, other than an earplug, or a container for a selected product. As a result, earplugs 10 may be used to advertise the non-earplug selected product. For example, earplugs 10 may be distributed to spectators at events that are typically very loud, such as popular music concerts or motor sport events (e.g., car races). It will be appreciated, however, that earplugs 10 could be distributed in any manner and used in any loud environment.

Earplugs 10 are shown with a cylindrical configuration so that, in combination with appropriate surface ornamentation 12, earplugs 10 may resemble can-type containers as are used for beverages (e.g., soft drinks or beer) and other liquid products (e.g., paints, oils, fuel additives, etc.). Surface ornamentation 12 is depicted generically as including a logo 14 and a product name 16. It will be appreciated, however, that such ornamentation details are merely exemplary and that surface ornamentation 12 may include either logo 14 or product name 16 alone or any other surface details to depict the selected product or product container. For example, surface ornamentation 12 may include only major visual components of the selected product or product container due to the relatively small size of earplugs 10.

Figure 2:
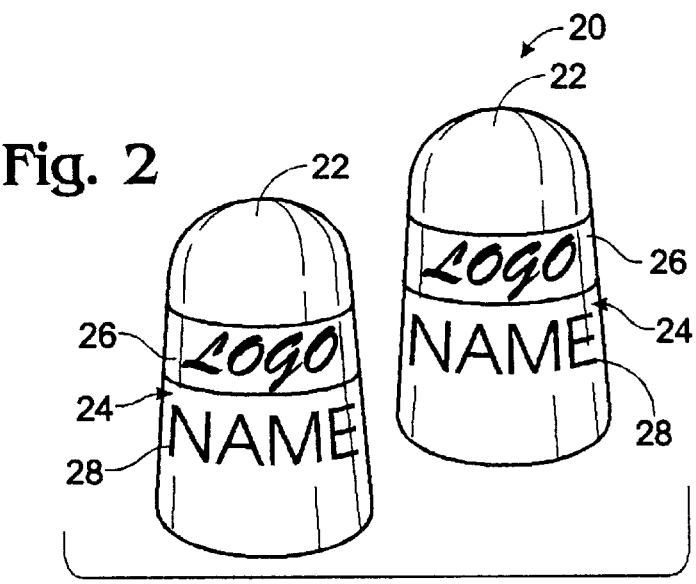
FIG. 2 is an isometric view of a second pair of exemplary earplugs according to the present invention.

FIG. 2 is an isometric view of another pair of exemplary earplugs 20 according to the present invention. Earplugs 20 are substantially the same as earplugs 10, except that earplugs 20 include a configuration that is slightly tapered and includes a rounded inner end 22 to facilitate insertion of earplugs 20 into a person's ear canal. Earplugs 20 also include surface ornamentation 24, with generic logo 26 and product name 28 that are the same as ornamentation 12. Earplugs 20 bear surface ornamentation 24 to resemble a product or product container that is actually cylindrical. Earplugs 20 illustrate that the resemblance between earplugs 20 and the selected product or product container can be imparted primarily by surface ornamentation 24 and that the configuration of earplugs according to the present invention may differ from the selected product or product container to accommodate earplug designs.

Figure 3:
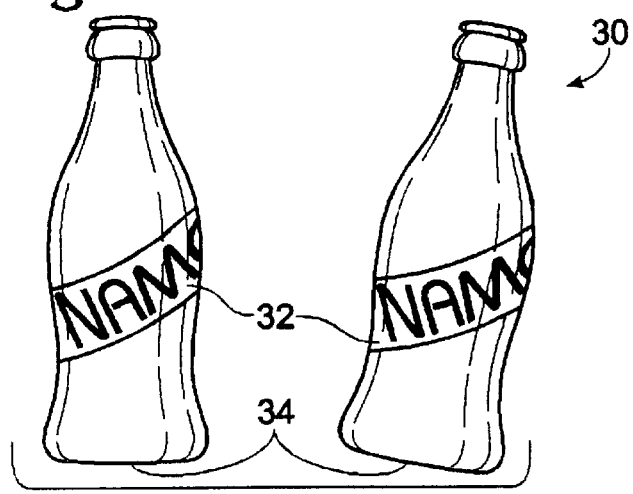
FIG. 3 is an isometric view of a third pair of exemplary earplugs according to the present invention.

FIG. 3 is an isometric view of another pair of exemplary earplugs 30 according to the present invention. Earplugs 30 are shown as including a generally non-cylindrical, arbitrary configuration that corresponds to a bottle, for example. Earplugs 30 also include surface ornamentation 32, which together with the configuration, resembles a selected product or product container. Earplugs 30 have base ends 34 that would be inserted into the person's ear canals.

With the resiliently expandable characteristics of the earplugs of the present invention, the surface ornamentation is applied with a printing material, such as ink, that adheres to the earplugs and is capable of flexing with the typical manipulation of such earplugs.

In view of the many possible embodiments to which the principles of our invention may be applied, it should be recognized that the detailed embodiments are illustrative only and should not be taken as limiting the scope of our invention. Rather, I claim as my invention all such embodiments as may come within the scope and spirit of the following claims and equivalents thereto.

What is claimed is:

1. A resiliently expandable noise-reducing earplug that is insertable into a person's ear canal, comprising:

surface ornamentation imprinted on the earplug, the surface ornamentation including a name or a logo for a selected product other than an earplug, the selected product having associated with it a selected product container configuration, the earplug further including a configuration resembling the selected product container configuration.

2. The earplug of claim 1 in which the surface ornamentation includes a name and a logo for the selected product.

3. The earplug of claim 2 in which the selected product container configuration and the earplug are generally cylindrical.

4. The earplug of claim 2 in which the selected product container configuration and the earplug are not generally cylindrical.

5. The earplug of claim 1 in which the selected product container configuration and the earplug are generally cylindrical.

6. The earplug of claim 1 in which the selected product container configuration and the earplug are not generally cylindrical.

* * * * *